(12) United States Patent
Lentine

(10) Patent No.: US 6,726,005 B2
(45) Date of Patent: Apr. 27, 2004

(54) DENTAL CAPSULE

(75) Inventor: Frank N. Lentine, Taylor, MI (US)

(73) Assignee: Kerr Corporation, Orange, CA (US)

( * ) Notice: Subject to any disclaimer, the term of this patent is extended or adjusted under 35 U.S.C. 154(b) by 128 days.

(21) Appl. No.: 09/951,698

(22) Filed: Sep. 13, 2001

(65) Prior Publication Data

US 2003/0047468 A1 Mar. 13, 2003

(51) Int. Cl.$^7$ .............................................. B65D 25/08
(52) U.S. Cl. ..................................... 206/222; 206/63.5
(58) Field of Search ............................... 206/219–222, 206/63.5

(56) References Cited

U.S. PATENT DOCUMENTS

| | | | |
|---|---|---|---|
| 2,754,590 A | | 7/1956 | Cohen |
| 2,778,360 A | | 1/1957 | Miskel |
| 3,327,710 A | | 6/1967 | Freeberg et al. |
| 3,404,811 A | * | 10/1968 | Cernei ......................... 222/83 |
| 3,415,360 A | * | 12/1968 | Baumann et al. ............ 206/222 |
| 3,425,598 A | * | 2/1969 | Kobernick ..................... 222/83 |
| 3,537,577 A | * | 11/1970 | Goupil ........................ 206/222 |
| 3,557,787 A | | 1/1971 | Cohen |
| 3,559,961 A | | 2/1971 | Bergendal |
| 3,595,439 A | * | 7/1971 | Newby et al. ................. 222/80 |
| 3,684,136 A | | 8/1972 | Baumann |
| 3,762,540 A | * | 10/1973 | Baumann et al. ............ 206/219 |
| 3,907,106 A | | 9/1975 | Purrmann et al. |
| 4,197,646 A | | 4/1980 | Morrison |
| 4,674,661 A | | 6/1987 | Herold |
| 4,871,261 A | | 10/1989 | Randklev |
| 4,973,168 A | | 11/1990 | Chan |
| 5,026,283 A | | 6/1991 | Osanai et al. |
| 5,396,986 A | * | 3/1995 | Fountain et al. ............. 206/219 |
| 5,509,530 A | | 4/1996 | Wilson |
| 5,710,194 A | | 1/1998 | Hammesfahr et al. |
| 5,746,313 A | | 5/1998 | Wilson |
| 5,976,507 A | | 11/1999 | Wong et al. |
| 5,981,620 A | | 11/1999 | Hammesfahr et al. |

FOREIGN PATENT DOCUMENTS

| | | | |
|---|---|---|---|
| FR | 2533820 A | 4/1984 | |
| GB | 1107894 A | 3/1968 | |
| WO | EP 0063 891 | 11/1982 | ............ A61C/5/06 |

* cited by examiner

Primary Examiner—Shian Luong
(74) Attorney, Agent, or Firm—Wood, Herron & Evans, L.L.P.

(57) ABSTRACT

A storage and mixing capsule 10 for separately storing a pair of ingredients therein and providing a structure for efficiently and reliably mixing the ingredients to form an amalgam. The capsule has two components: a first receptacle 12 and a second receptacle 14. The first receptacle 12 includes an interior compartment 16 for receiving an alloy and includes a piercing element 24 attached to a portion of the inner wall 26. The second receptacle 14 includes an interior compartment 30 for receiving mercury. The second receptacle 14 further includes a rupturable seal 38 disposed across the open bottom end 36 of the second receptacle 14. The capsule 10 further includes a conduit 54 extending from the capsule 10 which is used as a passageway for air to move from the interior of the capsule 10 to the exterior of the capsule 10 or for an inert gas to move from the exterior of the capsule 10 to the interior of the capsule 10 to create an interior atmosphere which prevents the oxidization of amalgam components. The second receptacle 14 is additionally adapted to be received by the first receptacle 12 and the two receptacles 12, 14 are movable relative one to another in order to bring the piercing element 24 into confronting relationship with the rupturable seal 38 in order to rupture the rupturable seal 38 and mix the components.

10 Claims, 3 Drawing Sheets

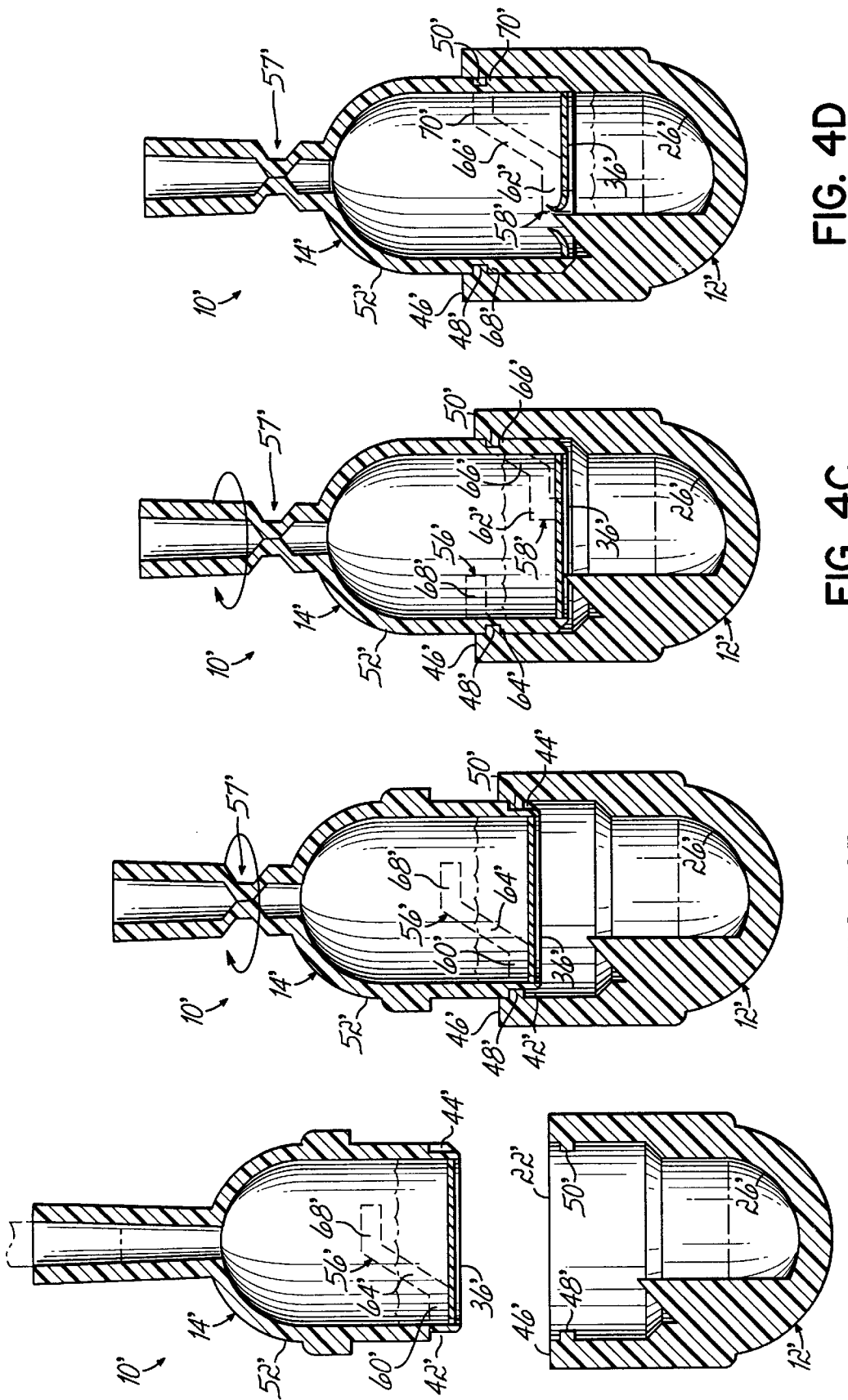

DENTAL CAPSULE

FIELD OF INVENTION

The present invention relates to a storage and mixing capsule for storing a plurality of ingredients which, in combination, form a mixture and, more particularly, to a capsule for storing such ingredients separate from one another and further providing for conveniently and efficiently mixing such ingredients into a composition.

BACKGROUND OF THE INVENTION

Dental amalgams are frequently used by dentists to fill in cavities drilled in a patient's teeth. Such amalgams typically include a combination of an alloy powder and an amount of liquid mercury. The alloy powder is typically a mix of gold or silver combined with copper, zinc, and/or tin. A temporarily pliable composition is formed immediately after these ingredients are mixed. This composition may be manipulated and formed and subsequently will harden into a solid composition. Thus, such compositions are ideal to serve as tooth fillings where a malleable substance is necessary to conform to the shape of the often irregular tooth cavity. After drilling to remove any decayed material from a tooth, a dentist will mix the ingredients of the amalgam capsule and insert the pliable amalgam into the cavity to fill the cavity. The amalgam then quickly hardens in the tooth to effectively fill the cavity and replace the removed decayed material.

Due to the above-mentioned properties of such dental amalgams, namely initially being soft and pliable but then quickly hardening to form a solid non-pliable mass, the ingredients must be stored separately until just prior to the time the dentist requires the amalgam to fill the cavity. Any premature mixing of the ingredients results in an unusable composition which hardens before it is needed and then must be discarded. Additionally, the individual ingredients may oxidize upon exposure to certain gases and air. Any oxidization of the ingredients also will result in an unusable composition which must be discarded.

Initially, in order to prevent premature mixing, the materials used to make amalgams were separately packaged. These materials were then dispensed into a mixing unit, which was then enclosed and mixing occurred by shaking. However, there were several drawbacks to these early versions of amalgam capsules, namely the oxidation of materials, along with the potential for a spill and problems with handling of the materials, particularly due to the hazardous nature of liquid mercury. As the amalgam capsules evolved, materials became pre-encapsulated with the alloy powder located in one section of the capsule and the mercury in another with a sealing mechanism included to prevent their mixture. During mixing, the seal would become disengaged or broken, thus allowing the ingredients to combine to form the dental amalgam. In these embodiments, the seal can be a foil or plastic that is pierced. Other times, the piercing can occur by the use of a separate object that becomes part of the mixing such as a free floating pestle. An example of one particular mixing capsule is disclosed in U.S. Pat. No. 3,841,467. This capsule includes a cylindrical container enclosed at its bottom end and open on its opposite end to receive an alloy. A circular plug rests on the upper edge of the container and has a central opening. A sealed plastic pouch filled with liquid mercury is placed between the upper surface of the plug and the inner top surface of the hollow cap which is in sliding engagement with the outer surface of the cylindrical container. Upon pressing the cap telescopically in an axial direction, the pouch is compressed with enough force to rupture the pouch to flow mercury through the central opening and into the container for mixing with the alloy. However, this capsule exhibits the drawback that the cap may easily be accidentally shifted or pressed downwardly to rupture the pouch and cause premature mixing of the amalgam.

Another such capsule is disclosed in U.S. Pat. No. 5,746,313 which discloses a mixing capsule including an inner storage capsule incorporating a cylindrical pestle. This pestle includes a cavity for storing a liquid component of the amalgam and has caps on both ends of the pestle. When the mixing capsule assembly is subjected to vibrational movement, the caps on the end of the pestle will impact the inner wall of the amalgam capsule thus freeing the liquid component stored therein to allow mixing with the alloy powders. Such apparatus is not free from shortcomings, however. For example, the capsule requires a relatively large number of intricate parts and is thus somewhat expensive to manufacture. Additionally, any accidental jostling of the capsule can result in premature mixing of the components.

Yet another such capsule is disclosed in U.S. Pat. No. 4,526,472. The capsule includes an outer capsule and an inner capsule, wherein the inner capsule includes a pair of open-ended cap members engaged with one another. These members form a stem and bore configuration with the stem being slidable within the bore and normally sealing the bore to trap an amalgam ingredient within the inner capsule. When the inner capsule is impacted against an interface with the outer capsule during shaking of the capsule, the stem is driven, relative to the bore, to open a passageway in order to allow the ingredient to flow into the outer capsule to mix with the ingredients stored in the outer capsule. The stem is relatively small in cross section and yet must come into direct contact with the interface of the outer capsule in order to open the passageway through the bore. Thus, in order to perform properly, the capsule requires the inner capsule follow a precise travel path during vibration. And again, these parts are manufactured at an increased cost.

As such, it will be appreciated that there is a need for a simple and efficient storage and mixing capsule to separately store the ingredients of a dental amalgam and to conveniently and reliably mix those ingredients when desired. Additionally, it would be desirable to have a capsule which incorporates a relatively small number of inexpensively-manufactured components and which is easy and efficient to assemble and use. Further, it would be desirable for such a capsule to facilitate quick and easy operation to combine such amalgam components for ease in mixing, and facilitate ease in accessing the amalgam once mixed. Further, it would be desirable to have a capsule which reduces or eliminates oxidization of amalgam ingredients. The present invention addresses these needs and eliminates the drawbacks of storage and mixing capsules of the prior art as will be described in greater detail below.

SUMMARY OF THE INVENTION

The present invention solves the problems and eliminates the drawbacks discussed above in the background of the invention. It does so by providing an efficient, inexpensive, and easy-to-use dental amalgam mixing capsule for separately storing a pair of ingredients therein and providing a structure for efficiently and reliably mixing the ingredients to form an amalgam. The amalgam capsule of the present invention includes a reliable means for storage of contents, either under vacuum or in the presence of an inert gas, to prevent oxidization. The amalgam capsule of the present invention also includes an improved structure for rupturing the seal between the cap and body of the amalgam capsule which efficiently and effectively prevents accidental premature mixing of the components.

In particular, the present invention provides a storage and mixing capsule having two components: a first receptacle and a second receptacle. The first receptacle includes an interior compartment for receiving an alloy. The first receptacle has a closed bottom end and an open top end. The open top end is further adapted to receive the lower, rupturably sealed end of the second receptacle. Finally, the first receptacle further includes a piercing element attached to a portion of the inner wall of the first receptacle and extending in a direction substantially parallel to the axis of symmetry of the first receptacle.

The second receptacle includes a closed top end and an open bottom end housing an interior compartment for receiving mercury. The open bottom end further includes a rupturable seal disposed across the open bottom end in a direction substantially perpendicular to the axis of symmetry of the second receptacle.

In a first aspect of the invention, the second receptacle further includes a conduit extending from the capsule in a direction substantially parallel to the axis of symmetry of the capsule. This conduit forms a passageway for air to move from the interior of the capsule to the exterior of the capsule so that a vacuum may be provided in the interior of the capsule to prevent the components of the amalgam from oxidizing. Alternatively, the conduit may form a passageway for a gas to move from the exterior of the capsule to the interior of the capsule. This gas is generally an inert gas which prevents oxidization of the components of the amalgam.

In use, the conduit facilitates providing a vacuum within the storage and mixing capsule by drawing air through said conduit from said interior of said capsule to said exterior of said capsule, or alternatively enables a gas to be provided in the storage and mixing capsule by forcing gas into the capsule by way of the conduit. After air has been removed and/or gas inserted, the conduit is collapsed in order to seal the interior of said capsule, thereby retaining the vacuum or gas within its interior.

In accordance with a second embodiment of the present invention, the open bottom end of the second receptacle is adapted to be received by the open top end of the first receptacle. When the second receptacle is received by the first receptacle, the two receptacles are movable relative to one another. The first receptacle further includes slots disposed substantially opposite one another proximal to the lip of the open top end of the first receptacle. Additionally, the first receptacle includes grooves which extend from the bottom of the slots around the circumference of the inner wall of the first receptacle. The second receptacle includes lugs disposed substantially opposite one another on the exterior wall of the second receptacle. These lugs are adapted to fit within the slots of the first receptacle when the first and second receptacles are engaged.

When the lugs are engaged in the slots near the lip of the first receptacle, the capsule is in a first position. The capsule can be moved to a second position by rotating the first and second receptacles relative one to another such that the lugs are slidably moved through the groove around the inner circumference of the first receptacle. When the lugs reach the end of the grooves, the capsule is in its second position. The groove on the first receptacle extends not only circumferentially around the inner wall of the first receptacle, but also is angled from the slot near the open top of the first receptacle towards the closed bottom end of the first receptacle. Thus, as the lugs are rotated through the grooves of the first receptacle from a first to a second position, the second receptacle is twisted down and into the first receptacle, thereby bringing the piercing element of the first receptacle into contact with the rupturable seal in the second receptacle. As this happens, the seal in the second receptacle is pierced allowing the liquid mercury to flow out and mix with the alloy components of the amalgam located in the first receptacle. This mixing may be enhanced by vigorously shaking the capsule. Following adequate mixing, the two receptacles are disengaged one from another and the amalgam may be removed and applied to a patient.

Thus, the present invention provides a two-piece capsule which successfully stores the ingredients of a dental amalgam separately, while allowing for their mixing when desired. Additionally, the capsule facilitates quick and easy operation for combining and mixing the amalgam components, along with ease in accessing the amalgam once formed. Also, the capsule of the present invention ameliorates the problem of oxidization of amalgam ingredients. Other features and advantages of the present invention will become apparent from the following detailed description, taken in conjunction with the accompanying drawings which illustrate by way of example the features of the invention.

BRIEF DESCRIPTION OF THE DRAWINGS

FIG. 4A is a cross-sectional view of an alternate embodiment of the storage and mixing capsule of the present invention depicting the first and second receptacles separate from one another;

FIG. 4B is a cross-sectional view of an alternate embodiment of the storage and mixing capsule depicting the first and second receptacles engaged in a first position;

FIG. 4C is a cross-sectional view of an alternate embodiment of the storage and mixing capsule depicting the second receptacle being rotated to be movably inserted into the first receptacle;

FIG. 4D is a cross-sectional view of an alternate embodiment of the storage and mixing capsule depicting the first and second receptacles of the storage and mixing capsule engaged in a second position.

DETAILED DESCRIPTION

As shown in FIGS. 1–4D, the present invention is embodied in a compartmentalized storage and mixing capsule 10.

The capsule 10 allows for storing, in partitioned fashion, the components of a mixture, such as a dental material and, when desired, for mixing such components to form a mixture, such as a dental material. In one embodiment, the dental material is a dental amalgam for use in the treatment of cavities. In alternate embodiments, other dental materials can be mixed. The features of the capsule 10 apply to any dental material that requires the mixing of two components just prior to application to the patient.

The storage and mixing capsule 10 of the present invention may be easily assembled, incorporates a minimum number of components, and is formed of relatively inexpensive thermoplastic materials so that manufacturing costs are held to a minimum. Additionally, the construction of the storage and mixing capsule 10 facilitates ease in operation for combining and mixing the components of the amalgam to quickly form the amalgam. Further, the structure of the storage and mixing capsule 10 facilitates quick and easy access to the mixed amalgam for its use. The storage and mixing capsule 10 of the present invention further prevents oxidization of the components of the amalgam during storage and is structured so as to reduce and eliminate the incidence of accidental premature mixing, such as often occurs with prior art capsules, such as was described in the background of the invention.

Figure 2B:
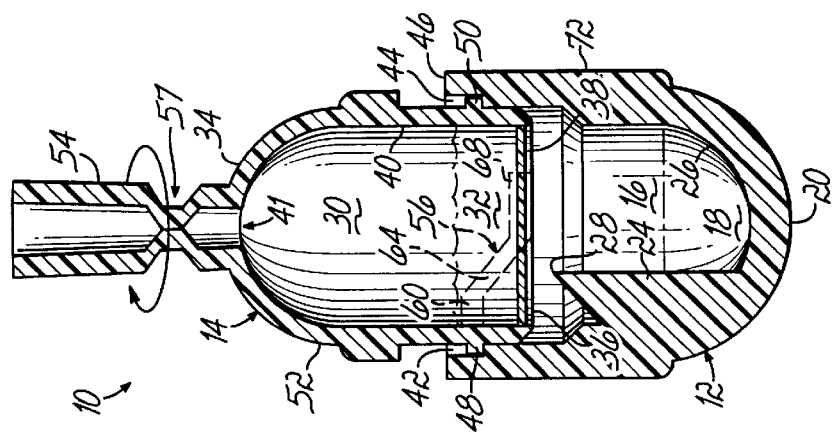
FIG. 2B is a cross-sectional view depicting the first and second receptacles of the storage and mixing capsule engaged in a first position.
Figure 2A:
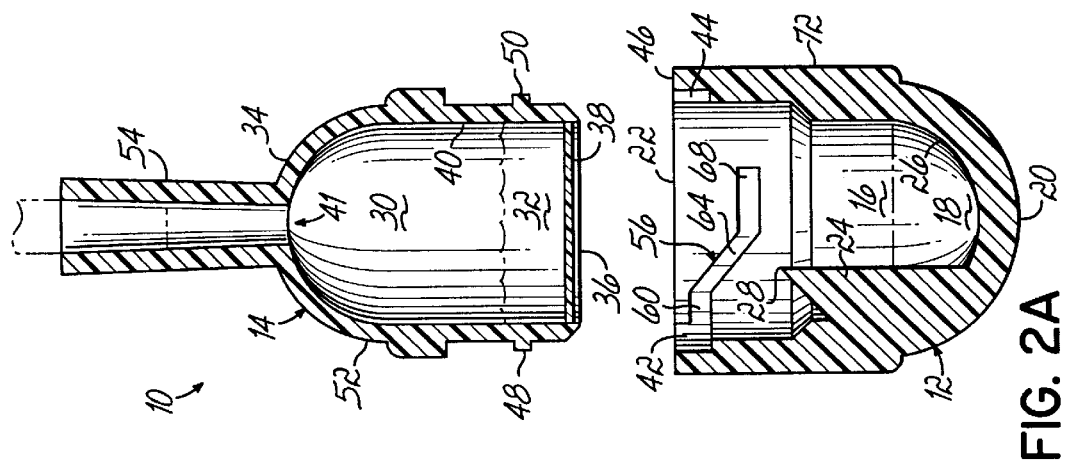
FIG. 2A is a cross-sectional view of the storage and mixing capsule of the present invention depicting the first and second receptacles separate one from another.
Figure 1:
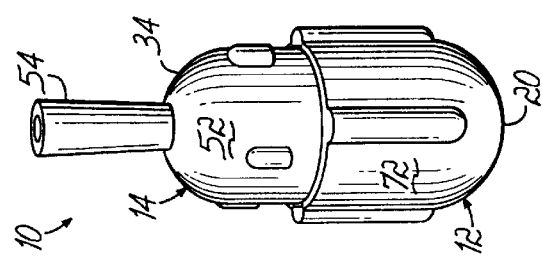
FIG. 1 is a perspective view of a storage and mixing capsule.

Referring to FIGS. 1 and 2A, the storage and mixing capsule 10 of the illustrated embodiment of the present invention includes a first receptacle 12 and a second receptacle 14. The first receptacle 12 and second receptacle 14 may be composed of a polymeric or thermoplastic material, such as polyvinylchloride (PVC), polyethylene, or a nylon, which provides sufficient rigidity and structural integrity to the storage and mixing capsule 10 while minimizing production and manufacturing costs. The aforementioned components of the capsule 10 may be formed using injection molding techniques well known to those skilled in the art. Additionally, such materials are selected to be chemically compatible with the chemical components of the amalgam or other material to be stored and mixed within the capsule 10 so as not to react with the chemical components.

The first receptacle 12 includes an interior compartment 16 for receiving a first component 18 of a dental material. This mixture may include one or more elements. These elements may be metals. In particular, these metals may be selected from, but are not limited to, gold, silver, copper, zinc, and tin. Often, the alloy is a mixture of gold or silver combined with either copper, zinc, or tin. The alloy may be in the form of a solid mass or may alternatively be in a form including, but not limited to, powdered or pelletized. In one embodiment, this first receptacle 12 is in a generally cylindrical configuration and has a closed bottom end 20 and open top end 22 which is adapted for receiving the second receptacle 14. In one embodiment, the closed bottom end 20 is of a generally concave shape. However, it is not necessary that the first receptacle 12 be cylindrical with a concave closed bottom end 20, as other shapes, such as a flat closed bottom end, will also suffice. The first receptacle 12 further includes a piercing element 24 which is formed integrally with the inner wall 26 of the first receptacle 12 and extends in a direction such that the longitudinal axis of the piercing element 24 is substantially parallel to the axis of symmetry of the first receptacle 12. The longitudinal axis of the piercing element 24 is that axis running along its length. The axis of symmetry of the first receptacle 12 is that axis about which the first receptacle 12 can be conceived to rotate and about which the first receptacle 12 is symmetrical.

Figure 3:
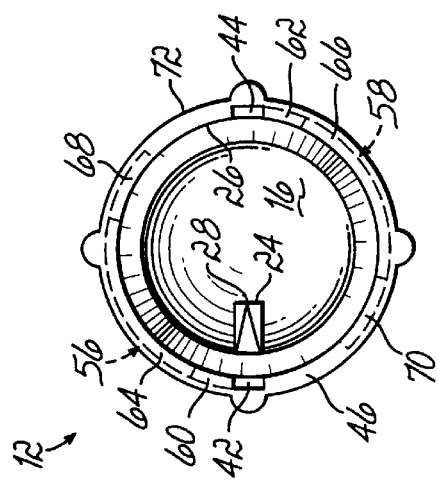
FIG. 3 is a top view of the first receptacle of the storage and mixing capsule of the present invention.
Figure 2D:
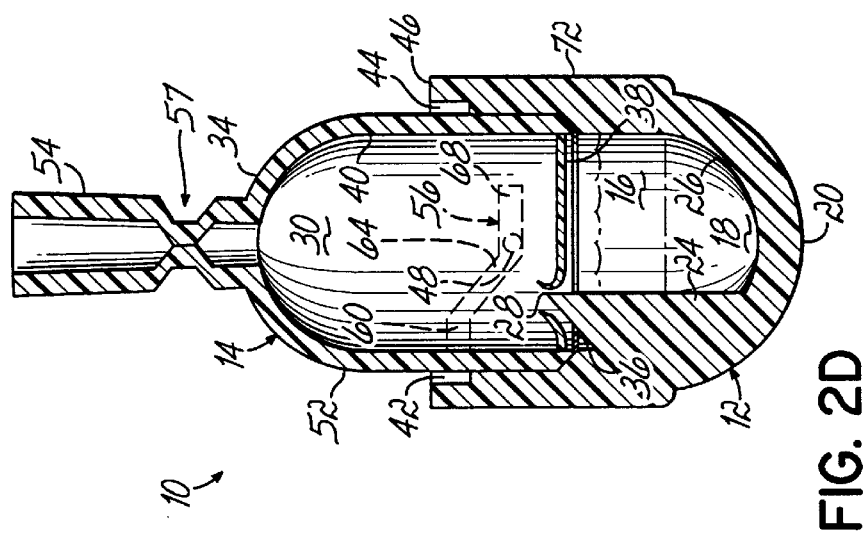
FIG. 2D is a cross-sectional view depicting the first and second receptacles of the storage and mixing capsule engaged in a second position.
Figure 2C:
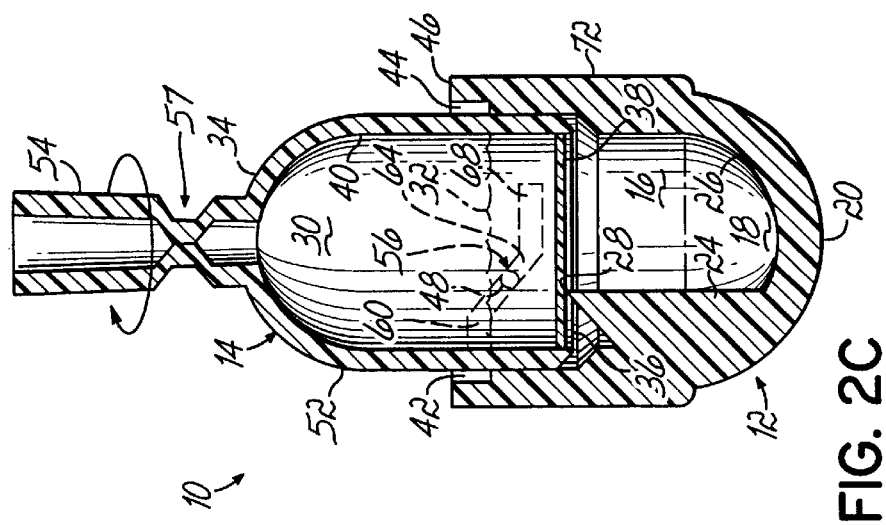
FIG. 2C is a cross-sectional view depicting the second receptacle of the storage and mixing capsule being rotated to be movably inserted into the first receptacle.

Referring now to FIGS. 1, 2A, and 3, in the illustrated embodiment, the piercing element 24 is in the general shape of a flat blade, having a generally rectangular configuration and being integral with the inner wall 26 of the first receptacle 12. The end of the blade proximal to the open top end 22 of the first receptacle 12 tapers to a point 28 of sufficient sharpness to rupture a seal. The piercing element 24 may be composed of the same material as the first and second receptacles 12, 14, as described above and may be formed using injection molding techniques well known to those skilled in the art. And, as described above, in certain embodiments, the piercing element 24 and first receptacle 12 may be integrally formed as one piece. In alternate embodiments, the storage and mixing capsule may include a plurality of piercing elements. Additionally, in alternate embodiments, the piercing element may be integral with or journaled to the closed bottom end rather than being integral with the inner wall. Additionally, in alternate embodiments, the piercing element may be journaled to the inner wall of the first receptacle.

The second receptacle 14 includes an interior compartment 30 for receiving a second component 32 of a dental material. In one embodiment, this second component 32 is mercury and is present in the capsule 10 in a liquid form. In use, this mercury combines with the alloy contained in the first receptacle 12 to form a dental amalgam. This second receptacle 14 is formed with a closed top end 34 and an open bottom end 36. The second receptacle 14 is of a generally cylindrical configuration with the closed top end 34 being of a generally concave shape. However, it is not necessary that the second receptacle 14 be cylindrical with a concave closed top end 34, as other shapes, such as a flat closed top end, will also suffice. A rupturable seal 38 is disposed within the interior compartment 30 of the second receptacle 14 proximal to the open bottom end 36 in a direction substantially perpendicular to the axis of symmetry of the second receptacle 14. The axis of symmetry of the second receptacle 14 is that axis about which the second receptacle 14 can be conceived to rotate and about which the second receptacle 14 is symmetrical. This seal 38 may be comprised of any material which can close off the interior compartment 30 of the second receptacle 14 in order to prevent the second component 32 from spilling out and/or prematurely mixing with the first component 18, and is subject to being ruptured by the piercing element 24 of the first receptacle 12. Such materials include, but are not limited to, aluminum foil, paper, paraffin, and plastic. In the illustrated embodiment, the rupturable seal 38 is attached along its peripheral edge to the inner wall 40 of the second receptacle 14. In alternate embodiments, the rupturable seal 38 can be attached to the tapered leading edge of the outer wall 73, or alternatively, may be attached to the outer wall 52. Such attachment may occur by any method known to those having skill in the art.

Referring now to FIGS. 2A–2D, the first and second receptacles 12, 14 are adapted to engage with one another to form the capsule 10 of the present invention. In the illustrated embodiment, the diameter of the open bottom end 36 of the second receptacle 14 is smaller than the diameter of the open top end 22 of the first receptacle 12 such that the open bottom end 36 of the second receptacle 14 may be inserted within the open top end 22 of the first receptacle 12. The first receptacle 12 further includes at least one slot disposed in its inner wall proximal to and continuous with the lip 46 of the open top end 22. In one embodiment, there may be a plurality of such slots. In the embodiment depicted in FIGS. 2A–2D, two slots 42, 44 are disposed substantially opposite one another along the circumference of the first receptacle 12. The second receptacle 14 includes at least one lug disposed on the exterior wall 52 of the second receptacle 14. In one embodiment, the second receptacle 14 may include a plurality of lugs. In the embodiment depicted in FIGS. 2A–2D, two lugs 48, 50 are disposed substantially opposite one another around the circumference of the exterior wall 52 of the second receptacle 14. The lugs 48, 50 and slots 42, 44 are configured to engage with one another with the lugs 48, 50 sized to insert into the slots 42, 44 as depicted in FIG. 2B. In this manner, the first and second receptacles 12, 14 are engaged with one another in a first position. It will be apparent to those of skill in the art that, in an alternate embodiment, the first receptacle may be sized to insert into the second receptacle with the slots disposed on the second receptacle, and the lugs disposed on the first receptacle.

In a first aspect of the present invention, depicted in the illustrated embodiment, the second receptacle 14 includes a conduit 54 extending from the second receptacle 14 in a direction substantially parallel to the axis of symmetry of the second receptacle 14. This conduit 54 is hollow and forms a passageway for air to be drawn out of the second receptacle 14 to create a vacuum within the second receptacle 14 in order to prevent oxidization of the dental material contained within the second receptacle 14. Closed top end 34 of second receptacle 14 will further include an orifice 41 disposed through the closed top end 34 at the intersection of top end 34 and conduit 54. Alternatively, the conduit 54 may be used for the introduction of a gas, and particularly of an inert gas, such as argon, from the exterior of the capsule 10 into the interior of the second receptacle. An interior atmosphere composed of such a gas will also prevent oxidization of the second component 32. It will be appreciated by those having skill in the art that other gases, and other inert gases such as xenon, neon, krypton, and radon may be used to prevent oxidization of the amalgam components. It will also be noted that in alternate embodiments the conduit may be located on the first receptacle or, alternatively, more than one conduit may be located on the capsule. Additionally, in alternate embodiments, the conduit may be located in a position other than parallel to the axis of symmetry of the capsule.

Referring to FIGS. 2A–2D, in use, the conduit 54 of the storage and mixing capsule 10 may be attached to a vacuum pump (not shown). As the storage and mixing capsule 10 is prepared, the first and second components 18, 32 are inserted into the first and second receptacles 12, 14 respectively.

The seal 38 is attached to the open end of second receptacle 14. The second component 32 is inserted through conduit 54 into inner cavity 30 via orifice 41 in the top end 34 of the second receptacle 14. The conduit 54 is then connected by means of a flexible tube (not shown) to the vacuum pump. The pump is started and pressure in the second receptacle 14 can be monitored by means of a pressure (vacuum) gauge (not shown). When the air has been removed from the second receptacle 14, creating a vacuum, the conduit 54 is collapsed by pinching, shown at 57, or some other method, whereupon the second component 32 of the dental material is retained in the second receptacle 14 under vacuum. The pump is then disengaged from the conduit 54.

In an alternate embodiment of the present invention, the flow of the vacuum pump may be reversed in order to introduce a gas, such as an inert gas, such as argon gas, into the second receptacle 14 of the storage and mixing capsule 10. The conduit 54 is then collapsed as described above. An inert gas such as argon will also prevent the oxidization of the first or first and second components 18, 32.

Figure 5:
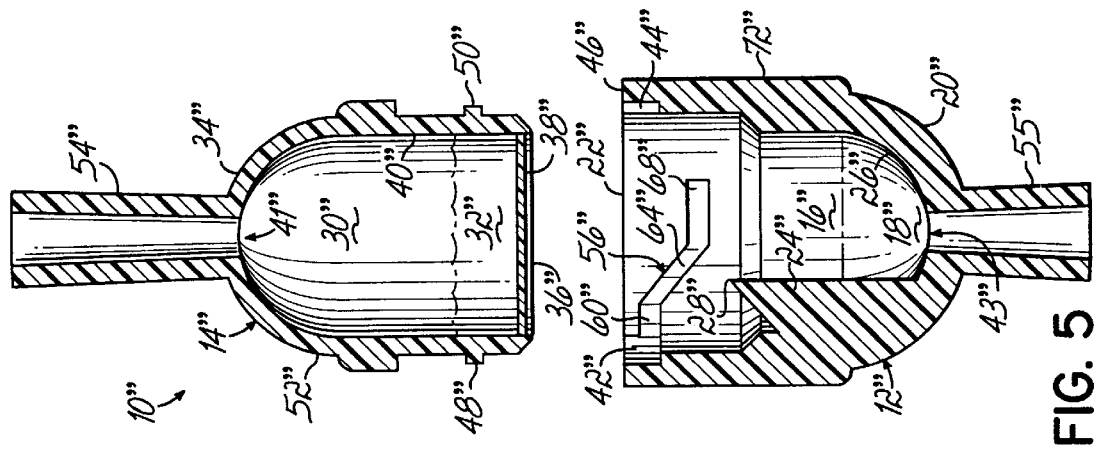
FIG. 5 is a cross-sectional view of an alternate embodiment of the storage and mixing capsule depicting conduits on the first and second receptacles.

In an alternate embodiment of the capsule 10" of the present invention including a plurality of conduits, depicted in FIG. 5, a first conduit 55" and a second conduit 54" may be located on the first and second receptacles 12", 14", respectively. These first and second conduits 55", 54" are hollow and form passageways for air to be drawn out of the first and second receptacles to create a vacuum within the capsule 10" in order to prevent oxidization of the first and second components 18", 32" contained within the capsule 10". In such an embodiment, the capsule 10" will include first and second orifices 43", 41" disposed through the surface of the closed bottom end 20" and closed top end 34", respectively. The first and second orifices 43", 41" are located at the intersection of the first receptacle 12" and first conduit 55", and at the intersection of the second receptacle 14" and the second conduit 54". Alternatively, the first and second conduits 55", 54" may be used for the introduction of the gas, and particularly an inert gas, such as argon from the exterior of the capsule 10" to the interior of the capsule 10". An interior atmosphere composed of such a gas will also prevent oxidization of the first and second components 18", 32". It will be appreciated by those having skill in the art that other gases, and other inert gases such as xenon, neon, krypton, and radon may be used to prevent oxidization of the amalgam components.

In the alternate embodiment of the present invention shown in FIG. 5, the capsule 10" may include first and second conduits 55", 54" for providing a vacuum or alternatively inert gas to each of the first and second receptacles 12", 14". In use, the sealed second receptacle 14" including rupturable seal 38" is inserted into the first position in engagement with first receptacle 12". A sealing tape or shrink wrap is then applied around the confronting surfaces of both first and second receptacles 12", 14". A first component 18" is inserted through first conduit into cavity 16" via orifice in the bottom end 20" of first receptacle 12". Likewise, the second component 32" is inserted through second conduit into cavity 30" via orifice in the top end 34" of second receptacle 14". The first and second conduits are then connected to a vacuum pump by means of a flexible tube (not shown). The pump is started and pressure in the first and second receptacles 12", 14" can be monitored by means of a pressure (vacuum) gauge (not shown). When the air has been removed from the first and second receptacles 12", 14" creating a vacuum, the first and second conduits 55", 54" are collapsed by pinching or some other method (not shown), whereupon the first and second components 18", 32" are retained in the first and second receptacles 12", 14" respectively under vacuum. The pump is then disengaged from the first and second conduits 55", 54".

Referring now to the illustrated embodiment of FIGS. 2A–3, in a second aspect, the present invention provides a structure to allow for efficient mixing of the first and second components while preventing their premature mixing. In the illustrated embodiment, the exterior wall 52 of the second receptacle 14 is formed with a pair of outwardly projecting lugs 48, 50 spaced a predetermined distance from the open bottom end 36 of the second receptacle 14 and spaced substantially opposite one another on the exterior wall 52 of the second receptacle 14. As described above, these lugs 48, 50 correspond to slots 42, 44 disposed in the inner wall 26 of the first receptacle 12 and are used to lock the first and second receptacles 12, 14 together to form the storage and mixing capsule 10. These lugs may be of any shape including, but not limited to, cylindrical, rectangular, and square. The exterior wall 52 of the second receptacle 14 may be formed with a rough outer surface, for instance by knurling, to provide a positive gripping surface for a clinician's fingers when the storage and mixing capsule 10 is in use.

The second receptacle 14 is formed with a closed top end 34 and an open bottom end 36 configured for receipt by the first receptacle 12 which includes the piercing element 24. The lugs 48, 50 of the second receptacle 14 are formed and configured for slidable receipt with the slots 42, 44 of the first receptacle 12. The first receptacle 12 further includes at least one groove disposed in the inner wall 26 of the first receptacle 12. In the illustrated embodiment of the present invention, the first receptacle 12 includes two grooves 56, 58. The grooves 56, 58 are integral with the distal end of the slots 42, 44 of the first receptacle 12. The grooves 56, 58 include three distinct sections: first flat sections 60, 62 which extend around a portion of the inner circumference of the first receptacle 12 in a direction substantially perpendicular to the axis of symmetry of the first receptacle 12; intermediate sections 64, 66 disposed along a portion of the inner circumference of the first receptacle 12 in a declining direction away from the slots 42, 44, toward the interior of the first receptacle 12; and second flat sections 68, 70 disposed around a portion of the inner circumference of the first receptacle 12 and substantially perpendicular to the axis of symmetry of the first receptacle 12. The second flat sections 68, 70 are substantially parallel to the first flat sections 60, 62 but are located distally from the open top end 22 of the first receptacle 12 as compared to the first flat sections 60, 62. The grooves 56, 58 are sized such that the lugs 48, 50 engaged with the slots 42, 44 will travel within the path formed by the grooves 56, 58 as the first and second receptacles 12, 14 are rotated relative to one another.

It will be apparent to those having skill in the art that in alternate embodiments of the present invention the lugs may be disposed on the inner surface of the first receptacle, and the grooves may be disposed about the exterior surface of the second receptacle. Referring to FIGS. 4A–4D, in such an alternate embodiment, the interior wall 26' of the first receptacle 12' is formed with a pair of inwardly projecting lugs 48', 50' spaced a predetermined distance from the open top end 22' of the first receptacle 12' and spaced substantially opposite one another on the interior wall 26' of the first receptacle 12'. These lugs 48', 50' correspond to slots 42', 44' disposed in the exterior surface 52' of the second receptacle 14' and are used to lock the first receptacle 12' and second receptacle 14' together to form the storage and mixing capsule 10'. The lugs 48', 50' of the first receptacle 12' are formed and configured for slidable receipt with the slots 42', 44' of the second receptacle 14'. The second receptacle 14' further includes grooves 56', 58', with each of the grooves 56', 58' being integral with one of the slots 42', 44' of the second receptacle 14'. The grooves 56', 58' include three distinct sections: first flat sections 60', 62' which extend around a portion of the outer circumference of the second receptacle 14' in a direction substantially perpendicular to the axis of symmetry of the second receptacle 14'; intermediate sections 64', 66' disposed along a portion of the outer circumference of the second receptacle 14' in a inclining direction away from the slots 42', 44' and toward the closed top end 34' of the second receptacle 14'; and second flat sections 68', 70' disposed around a portion of the outer circumference of the second receptacle 14' and substantially perpendicular to the axis of symmetry of the second receptacle 14'. The second flat sections 68', 70' are parallel to the first flat sections 60', 62' but are located distally from the open bottom end 36' of the second receptacle 14' as compared to the first flat sections 60', 62'. The grooves 56', 58' are sized such that the lugs 48', 50' engage with the slots 42', 44' will travel within the path formed by the grooves 56', 58' as the first receptacle 12' and second receptacle 14'0 are rotated relative to one another.

Referring to FIGS. 2A–3, operation of the mixing capsule 10 to mix the dental amalgam is described. To mix the dental amalgam, a clinician grasps the exterior wall 52 of the second receptacle 14, containing the second component 32, between his or her fingers in one hand and grasps the exterior wall 72 of the first receptacle 12 between the fingers of the other hand. The clinician then rotates the second receptacle 14 in one direction, such as clockwise in the illustrated embodiment, looking downwardly upon the closed top end 34 of the second receptacle 14, relative to the first receptacle 12 containing the first component 18 of the amalgam, to cause the lugs 56, 58 to move from the first position of their respective seats in the slots 42, 44 to follow the grooves 56, 58 to drive the second receptacle 14 downwardly from its first position relative to the piercing element 24 and first receptacle 12 to nest the respective lugs 56, 58 in the distal end of the second flat sections 68, 70 of the grooves 56, 58. As this happens, the second receptacle 14 is moved from the first position relative to the first receptacle 12 to the second position. As the second receptacle 14 is driven downwardly relative to the first receptacle 12, the rupturable seal 38 is cooperatively driven downwardly into the piercing element 24 in order to rupture the seal 38 separating the first and second components 18, 32. Once the seal 38 is ruptured, the second component 32 can disperse from the second receptacle 14 into the first receptacle 12.

Once the second component 32 has been introduced into the interior compartment 16 of the first receptacle 12, the clinician may place the capsule 10 in a mechanical vibrating apparatus or in the palm of one hand and shake the capsule 10 vigorously to mix the second component 32 with the first component 18. Thus, the mixing of the dental amalgam may be completed in a very short period of time.

Because the amalgam hardens very quickly, it is desirable that the clinician have easy and quick access to such amalgam for application within the cavity of the patient's tooth. To access the amalgam, the clinician may orient the mixing capsule 10 to its normal upright position with the second receptacle 14 in the upward orientation and rotate and pull upwardly on the second receptacle 14. As such, the respective lugs 48, 50 rotate back through and away from the grooves 56, 58 and respective slots 42, 44 to remove the second receptacle 14 from the open top end 22 of the first receptacle 12 such that the second receptacle 14 pulls away from the piercing element 24. Then the clinician has access to the mixed dental amalgam in the capsule 10.

While the invention has been disclosed by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

What is claimed is:

1. A storage and mixing capsule comprising:
   a first receptacle including an interior compartment for receiving a first component of a dental material, said first receptacle having a bottom end and a top end, said top end adapted for receiving a second receptacle; and
   a second receptacle including an interior compartment for receiving a second component of a dental material, said second receptacle having a top end and a bottom end, said bottom end adapted to be received by said first receptacle;
   wherein one of said first receptacle and said second receptacle further includes a piercing element disposed on an inner wall of one of said first receptacle and said second receptacle, and the other of said first receptacle and said second receptacle further includes a rupturable seal;

wherein said first receptacle is rotatably movable relative to said second receptacle; and wherein said capsule includes a first position and a second position, wherein when said capsule is in a first position, said piercing element overlies said rupturable seal and when said capsule is brought into said second position by rotating one of said first and second receptacles relative to the other, said piercing element is in confronting relationship with said rupturable seal in order to pierce said rupturable seal.

2. The capsule of claim 1 wherein said first receptacle includes an inner wall and further includes at least one slot disposed in the inner wall of said first receptacle proximal to and continuous with a lip of the open top end of said first receptacle.

3. The capsule of claim 2 wherein said first receptacle further includes at least one groove disposed in the inner wall of said first receptacle, said groove being integral with said at least one slot.

4. The capsule of claim 3 wherein said second receptacle includes an exterior wall and further includes at least one lug disposed on the exterior wall of said second receptacle.

5. The capsule of claim 4 wherein when said capsule is in said first position, said lug is disposed in said slot.

6. The capsule of claim 4 wherein said lug is further adapted to be slidably compatible with said groove as said capsule is being moved from said first to said second position by movement of said first receptacle relative to said second receptacle.

7. The capsule of claim 4 wherein when said capsule is in said second position, said lug is disposed in said groove distal from said at least one slot.

8. The capsule of claim 1 further including a conduit extending from the capsule, wherein said conduit forms a passageway to transport gas between one of the interior compartments and the exterior of the capsule.

9. The capsule of claim 8 wherein said conduit forms a passageway to transport said gas from one of the interior compartments of the capsule to the exterior of the capsule.

10. The capsule of claim 8 wherein said conduit forms a passageway to transport said gas from said exterior of said capsule to one of the interior compartments of the capsule.

* * * * *